United States Patent [19]

Feinman et al.

[11] Patent Number: 4,830,615
[45] Date of Patent: May 16, 1989

[54] TWO-GRIT CUTTING AND POLISHING INSTRUMENTS

[76] Inventors: Ronald A. Feinman, 5310 London Dr. NW, Atlanta, Ga. 30327; Ronald E. Goldstein, 5135 Marbury Cir., NW, Atlanta, Ga. 30327; David A. Garber, 325 Benita Trace, Atlanta, Ga. 30328

[21] Appl. No.: 69,158

[22] Filed: Jul. 2, 1987

[51] Int. Cl.$^4$ .................................................. A61C 3/06
[52] U.S. Cl. ..................................... 433/166; 433/142; 433/229
[58] Field of Search ................. 433/166, 165, 142, 224

[56] References Cited

U.S. PATENT DOCUMENTS

| | | | |
|---|---|---|---|
| 750,639 | 1/1904 | Graft | 433/166 X |
| 959,054 | 5/1910 | Glover | 433/166 X |
| 2,842,844 | 7/1958 | Seal | 433/166 |
| 3,142,138 | 7/1964 | Kean et al. | 433/166 X |
| 3,267,623 | 8/1966 | Block | 433/142 X |
| 4,030,198 | 6/1977 | Gerber | 433/142 |
| 4,178,689 | 12/1979 | Nash | 433/166 |
| 4,187,082 | 2/1980 | Guerra | 433/229 |
| 4,447,208 | 5/1984 | Kawai | 433/166 |
| 4,563,152 | 1/1986 | McClure | 433/142 X |
| 4,690,642 | 9/1987 | Kyotani | 433/142 |

OTHER PUBLICATIONS

Pfingst & Company Inc., 1983 Catalog, No. 33, pp. 8, 17, 18 and 22-28.

*Primary Examiner*—Larry Jones
*Attorney, Agent, or Firm*—Sherman and Shalloway

[57] ABSTRACT

Disclosed herein are embodiments of dental instruments having their surfaces formed with abrasive coatings which are used for both cutting and polishing functions. In each of the instruments disclosed herein, the abrasive surface consists of a plurality of regions with each region having a distinct degree of coarseness or fineness different from the degree of abrasion of which other regions consist. In some of the instruments, the finer abrasiveness is on the end of the instrument whereas the coarser region is away therefrom, whereas in other instruments the coarser region is at the end. Other embodiments are disclosed which have alternating regions of coarseness and fineness. In some of the instruments, the interfaces between the regions define distinct changes in abrasiveness whereas in other instruments, these interfaces define gradual changes in abrasiveness.

12 Claims, 2 Drawing Sheets

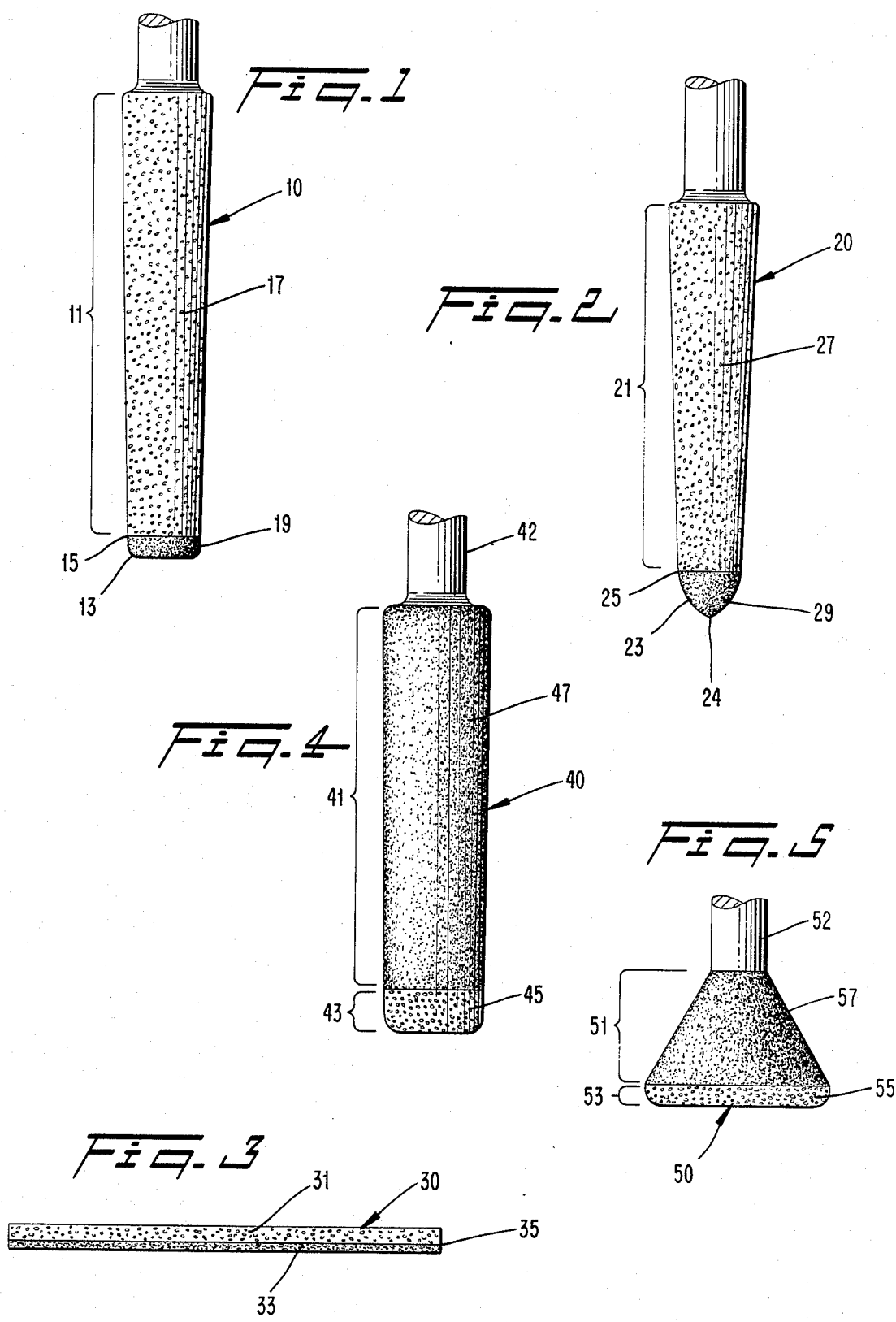

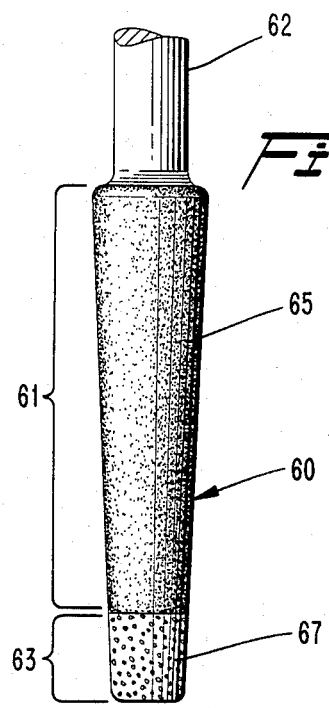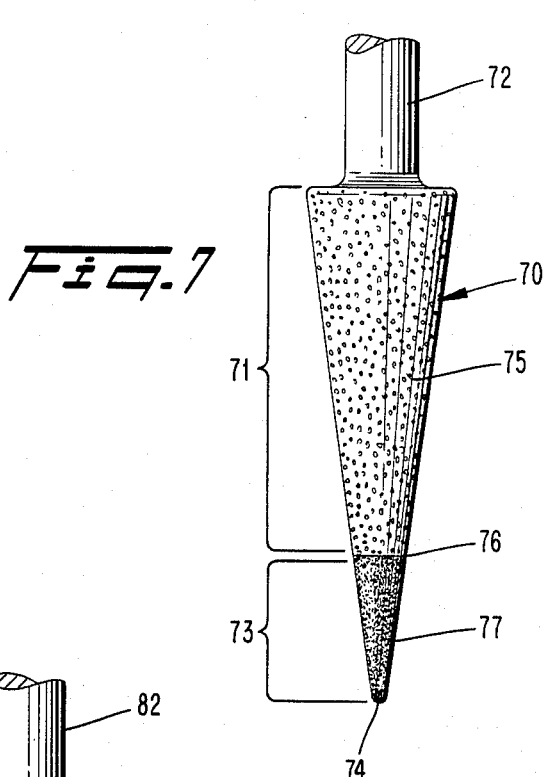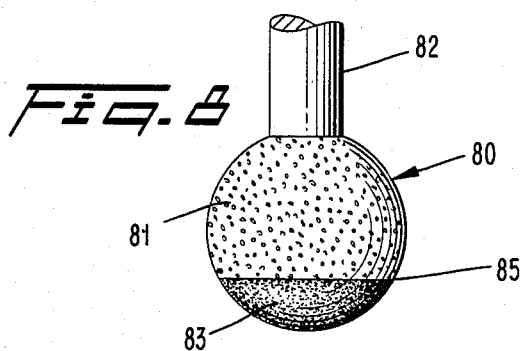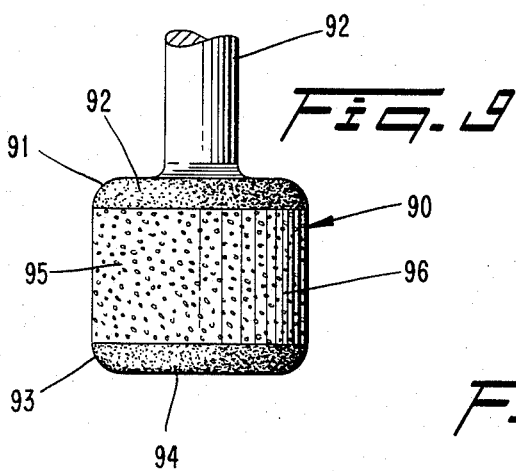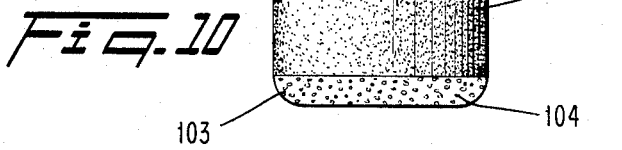

TWO-GRIT CUTTING AND POLISHING INSTRUMENTS

BACKGROUND OF THE INVENTION

In the prior art, impregnated instruments which are used for cutting or polishing only have a single degree of abrasiveness throughout the work surfaces of the instruments. Thus, when, for example, a dentist must prepare a margin on a tooth, a first instrument must be used having a coarsely abrasive surface so that material may be removed from a crown, for example, to provide the proper configuration whereupon a second instrument with a fine abrasiveness may be used to polish the areas where the coarsely abrasive tool was used to remove material. Thus, a need has developed for dental instruments wherein each instrument includes regions of unique differing abrasiveness, which regions are adjacent one another and merge together at an interface.

Applicants are aware of the following United States patents:
U.S. Pat. No. 2,453,696 to Brooks
U.S. Pat. No. 4,019,254 to Malmin
U.S. Pat. No. 4,190,958 to Martin, et al.
U.S. Pat. No. 4,518,356 to Green None of these patents teaches the concept of differing abrasive surfaces on a single tool although both Malmin and Martin, et al. disclose tools having abrasive areas and areas without abrasiveness. In applicant' view, a tool with abrasive and non-abrasive areas is no different than a tool with a single abrasive property throughout since neither tool provides the possibility of treating a tooth surface with two degrees of abrasiveness on a single tool.

U.S. Pat. No. 4,338,748 to Elbel discloses a metal machining grinding tool having matrix bonded abrasive grains having a hardness which varies over the grinding area. The present invention is believed to distinguish from the teachings of this patent as teaching different degrees of abrasiveness in different regions of a single tool rather than different degrees of hardness.

Further, a product is known to applicants which is manufactured by the 3M Company and which comprises an elongated flexible plastic strip having aluminum oxide coatings at each end separated by an uncoated central portion with these coatings being in two different degrees of abrasiveness. The present invention is believed to clearly distinguish from the teachings of this product as including surfaces of differing degrees of abrasiveness which are immediately adjacent one another and which merge into one another.

Finally, German Gebrauchsmuster 8411017 discloses an instrument in FIG. 3 which includes a finely abrasive surface 18 and a coarsely abrasive surface 16 meeting at a jagged interface. The present invention is believed to be distinct from the teachings of this document since the present invention defines a clear transition zone between regions of differing abrasiveness which makes the present invention easier to use and more effective than the invention disclosed in the German document.

SUMMARY OF THE INVENTION

The present invention overcomes the deficiencies found in the prior art and provides a series of dental instruments each of which incorporates the teachings of the present invention, to provide such instruments in a clearly improved form with increased versatility as well as effectiveness. The present invention includes the following interrelated embodiments:

(a) A first embodiment of the present invention comprises modifications to a tapered diamond stone instrument having a rounded tapered end. In modifying this instrument in accordance with the teachings of the present invention, a coarse surface is formed throughout the proximal length of the instrument and adjacent the distal end thereof, proximal of the curved portion of the end, a fine or micro-fine abrasive surface is provided.

(b) A second instrument which is modified in accordance with the teachings of the present invention is a tapered diamond chamfer instrument. This instrument is tapered at its proximal and at the distal end has a curved portion terminating at a rounded point. In modifying this instrument in accordance with the teachings of the present invention, the curved portion with rounded point is provided with a fine or extra fine abrasive surface whereas the proximal remainder of the instrument is provided with a coarse abrasive surface.

(c) A further embodiment of the present invention constitutes modifications to an elongated flexible strip which is utilized in finishing surfaces between adjacent teeth. Such a strip is modified in accordance with the teachings of the present invention so that a coarse abrasive surface is provided along the entire longitudinal length of the strip and partially along the height direction thereof while a fine abrasive surface is provided along the entirety of the longitudinal extent thereof and for the rest of the height thereof.

(d) In a further embodiment, instruments which are utilized to open up inner tooth surfaces in restoration procedures may be modified in accordance with the teachings of the present invention. These instruments may be elongated cylindrical instruments or may have an inverted taper with the widest portion distal from the drive shaft thereof. In modifying these instruments in accordance with the present invention, the end of the instrument distal from the drive shaft is provided with a coarse or extra coarse abrasive surface with the proximal remainder of the instrument being provided with a fine or micro-fine abrasive surface.

(e) The teachings of the present invention may also be used on instruments designed for endodontic use, which instruments are utilized in preparing root canal chambers and canals for posts. In such instruments, modification may be undertaken in accordance with the teachings of the present invention to provide the distal tip of the instrument with a coarse abrasive surface while the proximal remainder of the surface of the instrument is provided with a fine or micro-fine abrasive surface.

(f) In accordance with the teachings of the present invention, the transition region between the different degrees of abrasiveness may be sudden or gradual, as desired. Furthermore, the teachings of the present invention while mainly applied to diamond-coated instruments may just as effectively be applied to instruments which use abrasive coatings of aluminum oxide and carborundum, diamond and carborundum and silicone dioxide and aluminum oxide.

(g) The teachings of the present invention may also be applied to dental instruments in the shape of an inverted Christmas tree, in particular, of conical shape and terminating at a point. Such instruments are normally provided to create a margin on a tooth in preparation for retention. Such instruments may be modified in accordance with the teachings of the present invention by providing a fine or micro-fine abrasive surface on the distal tip thereof and by providing a coarse or extra coarse abrasive surface on the proximal portions thereof.

(h) Finally, the teachings of the present invention may be applied to spherical dental instruments which are utilized in creating margins as well as interior filling-retentive surfaces. In such dental instruments, the proximal end adjacent the drive shaft may be provided with a coarse abrasive surface, while the distal end of the instrument may be provided with micro-fine abrasive surfaces.

Accordingly, it is a first object of the present invention to provide a improved abrasive surface for dental instruments.

It is still further object of the present invention to provide such an improved abrasive surface for dental instruments which includes surfaces of different abrasiveness in different regions of the instrument so that a single dental instrument may perform the functions which were previously attributable to a plurality of instruments which were used sequentially during certain dental procedures.

It is a yet further object of the present invention to provide such a new and improved abrasive surface in differing configurations on the various dental instruments as described hereinabove.

It is a still further object of the present invention to provide such as surface with either gradual or sudden transition zone between the degrees of abrasiveness formed thereon.

These and other objects, aspects and features of the present invention will be better understood from the following detailed description of the preferred embodiments when read in conjunction with the appended drawing figures.

BRIEF DESCRIPTION OF THE DRAWINGS

FIG. 1 shows the teachings of the present invention when applied to a tapered diamond stone instrument.

FIG. 2 shows the teachings of the present invention when applied to a tapered diamond chamfer instrument.

FIG. 3 shows the teachings of the present invention when applied to an elongated flexible strip.

FIGS. 4 and 5 show the teachings of the present invention when applied to instruments designed to open up, enlarge or refine the tooth in restorative treatments.

FIG. 6 shows the teachings of the present invention when applied to dental instruments designed for use in preparing root canals.

FIG. 7 shows the teachings of the present invention when applied to a dental instrument designed to create a bevel or put a margin on a tooth.

FIG. 8 shows the teachings of the present invention when applied to a spherical dental instrument.

FIGS. 9 and 10 show the teachings of the present invention when applied to wheel-shaped dental instruments used for creating depth cuts.

SPECIFIC DESCRIPTION OF THE PREFERRED EMBODIMENTS

With reference first to FIG. 1, a first embodiment of the present invention is illustrated. Therein, a tapered diamond stone instrument 10 is seen to include a proximal tapered shaft portion 11 and a distal tapered rounded end portion 13 which is formed below an interface 15 between the shaft and end. The shaft portion 11 has a surface 17 which has a coarse abrasive surface thereon whereas the distal tapered round end 13 has a surface 19 thereon which has a fine or micro-fine abrasive surface thereon. This instrument may be used to create a margin on a tooth with the stem portion 11 being used to remove relatively large amounts of material and with the end 13 being utilized to polish those surfaces which have first been formed using the stem portion 11 with its coarse abrasive surface 17.

FIG. 2 shows a second embodiment of the present invention as applied to a tapered diamond chamfer instrument 20 which is seen to include a tapered stem portion 21, a rounded end 23 terminating at a rounded point 24, and an interface 25 between the stem 21 and end 23. As seen in FIG. 2, the stem portion 21 has a surface 27 which is coarsely abrasive whereas the end 23 has a surface 29 thereon having an abrasive surface which is of fine or micro-fine consistency. The instrument 20 is utilized to create a chamfer margin on a tooth and the coarsely abrasive surface 27 of the stem 21 is utilized to remove material from the tooth while the end 23 with its fine or micro-fine abrasive surface 29 is utilized to polish those surfaces which have already been formed through engagement with the coarsely abrasive surface 27.

FIG. 3 shows an example of an elongated flexible strip 30, preferably made of a flexible spring steel and having a coarsely abrasive surface 31 extending its entire length and adjacent thereto having a finely abrasive surface 33 also extending the entire length thereof, which surfaces merge at an interface 35. This strip 30 may be utilized for interproximal finish of composite and porcelain materials or may be utilized for any other finishing technique, especially those which occur between teeth whether they be natural or be caps or crowns.

FIG. 4 shows a cylindrical or slightly tapered instrument 40 having a drive shaft 42 a proximal end 41 and a distal end 43. As seen, the distal end 43 has an abrasive surface which may be characterized as of coarse consistency while the proximal surface 41 has a surface 47 which may be characterized as having a micro-fine or fine abrasive quality. Such an instrument is utilized to open up the tooth in restorative treatment and is commonly utilized to removed old fillings and thereafter to finish the inside surfaces of the tooth.

FIG. 5 shows an inverted tapered instrument 50 which is used for similar purposes as the instrument 40 and which includes a drive shaft 52, a proximal end 51 and a distal end 53 with the distal end 53 having a coarsely abrasive surface 55 and with the proximal end 51 having a surface 57 which is finely abrasive.

With reference to FIG. 6, a tapered endodontic dental instrument made in accordance with the teachings of the present invention is seen to include an elongated tapered shape with a drive shaft 62, a proximal and slightly tapered portion 61 and a distal slightly tapered end 63. The proximal portion 61 is seen to include an abrasive surface 65 of fine consistency whereas the distal end has an abrasive surface of coarse consistency. This instrument is utilized to prepare root canal chambers and canals for the insertion of posts. Through the teachings of the present invention, this instrument may be used with the end portion 63 forming the chamber or canal due to its coarsely abrasive surface 67, and with the proximal portion 61 smoothing the surfaces of the chamber or canal due to its finely abrasive surface.

FIG. 7 shows a conical inverted Christmas tree shaped dental instrument 70 having a drive shaft 72, a drastically tapered proximal end 71 and a similarly tapered distal end 73 terminating at a point 74. An interface 76 exists between the proximal and distal portions. With reference to FIG. 7, the proximal portion 71 has a surface 75 of coarsely abrasive consistency whereas the distal portion 73 has a surface 77 of a micro-fine abrasive consistency. The tool 70 is utilized to create a micro-fine margin on the surfaces of a tooth in preparation for final retention in the mouth.

With reference to FIG. 8, a spherical tool 80 is seen to include a drive shaft 82, a proximal end 81 and a distal end 83 merging at an interface 85. The proximal end 81 is seen to have an abrasive surface of coarse quality whereas the distal end has an abrasive surface of micro-fine quality. This tool is utilized to grind internal surfaces of a tooth in preparation for retention and the provision of levels of abrasiveness on one tool avoids the use of a plurality of tools.

FIG. 9 shows a wheel-shaped tool 90 which is designed to be used for creating depth cuts. This tool is seen to include a drive shaft 92, a proximal end 91, a distal end 93 and a centrally located portion 95 between the proximal 91 and distal end 93. As seen in the figure, the proximal end 91 includes a surface 92 of finely abrasive quality, the distal end 93 includes an abrasive surface 94 of finely abrasive quality and the central portion 95 includes an abrasive surface 96 of coarse quality.

FIG. 10 shows a wheel-shaped instrument 100 which is similar in shape to the instrument 90, however, the abrasive qualities of the surfaces thereof have been reversed. The instrument 100 includes a drive shaft 102, a proximal end 101, a distal end 103 and a central portion 105. The proximal and distal ends 101 and 103, respectively, have respective surfaces 102 and 104 of coarsely abrasive quality, whereas the central portion 105 has a surface 106 of finely abrasive quality.

The present invention must be considered in light of several factors. Firstly, each of the above described embodiments discloses at least two different surface regions of different abrasive qualities. The embodiments of FIGS. 9 and 10 show three such surfaces of alternating abrasive qualities. It should be understood that the transition regions between the different regions of differing abrasive qualities may be sudden or, if desired, may be of gradually changing abrasive quality. Furthermore, it is stressed that one of the main reasons for providing different abrasive qualities on one instrument is to avoid the necessity of the use of a plurality of different instruments in performing a single operation. As is well known, most dental offices include rotary tool systems wherein only a single tool head is available in any one room so that without the teachings of the present invention, when a dentist must perform an operation with a single type of tool but needing a plurality of abrasive qualities, the dentist must continually replace the tool portion from the head with a tool of the desired abrasive quality. These procedures slow the dentist's work and may cause the dentist to lose concentration. In accordance with the teachings of the present invention, by combining different abrasive qualities on a single tool, such deficiencies are avoided.

If desired, for ease of identification of the qualities of the abrasive surfaces, surfaces of differing abrasive qualities may be color coded so that the dentist may easily determine which region on any given instrument is of a particular abrasive quality.

As should be understood by those skilled in the art, when a ceramic crown is being prepared for insertion in the mouth, it is desirable to form a shoulder with a rounded axial gingival line angle. This shoulder finish line should be smoothly finished or polished with a fine diamond or carbide rotary instrument or hand instrumentation to provide for an improved seal where the crown abuts the tooth.

Furthermore, the axial wall should be rapidly reduced with a minimum of heat production and should not be smoothly polished, but rather should have coarse rotary instrument striations to aid in retention. Preferably, the preparation should extend no more than one millimeter below the free gingival margin and should be mildly tapered.

As is well known in the prior art, in order to prepare a ceramic crown in accordance with the parameters set forth hereinabove, as many as three to six different rotary instruments must be utilized. The present invention wherein a plurality of different abrasive qualities are provided on a single instrument should enable a skilled dentist to prepare a ceramic crown with all the above described parameters through the use of a single instrument. An instrument which can perform all of these operations is that which is set forth in FIG. 1. The instrument described in FIG. 1 is designed to rapidly reduce enamel and to produce and shoulder right at the gingival margin and thereafter to extend gently into the sulcus at a slower rate by using the end of the tool with its fine grit to produce this refined margin.

In the preferred embodiment of such instrument 10, the radius of the rounded corner is approximately one millimeter so that it gives the operator a definitive guide as to how deep the instrument is to extend into the sulcus.

The advantage of the use of an instrument such as that which is set forth in FIG. 1 over, for example, a chamfer instrument such as that which is designated by the reference numeral 20 in FIG. 2 is that a chamfer is rounded at the end so that ideally one should not extend the bur toward the pulp more than a maximum of half the width of the bur. If this is done, a rounded trough will be created in the gingival area which will have to be leveled out at a later stage through the use of a further instrument. Also, it is difficult to gauge how deep one is going with a chamfer instrument. Thus, if one does not sink the bur more than halfway into the enamel and dentin, then the instrument only needs to be about two millimeters in diameter at the tip to develop a chamfer of 1.3 millimeters in width. What this means is that there will be constant rotary abrasion of the tissue during such operation.

The use of a two-grit instrument such as those which are disclosed hereinabove will facilitate entering the sulcus without any gingival injury because the rounded radius on the tip of the instrument 10 will avoid the gingival soft tissue. Furthermore, the vortex created by rotation of the bur helps move the tissue laterally away therefrom.

On the other hand, the chamfer instrument 20 seen in FIG. 2 is often considered to be the desired instrument for use in preparing base metal alloy ceramo-metal restorations as well as for some forms of noble alloy restorations. This chamfer finish line should once again be smooth, finished and refined with a fine form of rotary instrument while the axial wall, as discussed hereinabove, should not be polished but rather should have coarse striations to aid in retention. In addition, the desired instrument facilitates rapid cutting of the axial wall without the disadvantageous production of heat.

The other instruments described hereinbelow are well known in their general shapes and configurations to those skilled in the art and the reasons for the particular surface abrasiveness as shown in FIGS. 3–10 should be self evident to those skilled in the art with this disclosure before them.

Accordingly, an invention has been disclosed in terms of several exemplary embodiments which fulfills each and every one of the objectives as set forth hereinabove and which provides an improved set of instruments for use by a dentist. Of course, various changes, modifications and alterations in the teachings of the present invention may be contemplated by those skilled in the art without departing from the intended spirit and scope thereof. For example, while the interface between regions of differing abrasiveness on the instruments disclosed hereinabove has been shown as substantially perpendicular to the rotation axis of the instrument, of course, this interface could be obliquely related to the rotation axis. Accordingly, it is intended that the present invention only be limited by the terms of the appended claims.

We claim:

1. An improved dental instrument comprising:
   (a) an implement having an abrasive surface thereon adapted to engage tooth surfaces, said implement having an axis and comprising a rotary tool adapted to rotate about said axis;
   (b) said abrasive surface comprising a first region having a texture of a first degree of abrasiveness and a second region having a texture of a second, different degree of abrasiveness, said regions being adjacent one another, said first region being proximal of said implement and said second region being distal of said implement, and said regions merging at an interface disposed substantially perpendicular to said axis.

2. The invention of claim 1, wherein said instrument comprises a tapered diamond stone, said first region having a coarser degree of abrasiveness than said second region.

3. The invention of claim 1, wherein said instrument comprises a tapered diamond chamfer instrument, said second region being at a tapered end thereof and having a micro-fine degree of abrasiveness.

4. The invention of claim 1, wherein said implement is substantially cylindrical, said first region having a fine degree of abrasiveness and second region having a coarse degree of abrasiveness.

5. The invention of claim 1, wherein said implement is substantially conical with a taper thereof being wider at said second region, said second region having a coarse degree of abrasiveness and said first region having a finely abrasive consistency.

6. The invention of claim 1, wherein said implement comprises a tapered endodontic device having said first region of finely abrasive consistency and said second region of coarsely abrasive consistency.

7. The invention of claim 1, wherein said implement is substantially spherical with said first region being of coarser consistency than said second region.

8. The invention of claim 1, further wherein said abrasive surface further comprises a third region on a side of said second region opposite to the side thereof on which said first region is located, said first and third regions having substantially equal degrees of abrasiveness.

9. The invention of claim 8, wherein said first and third regions have a finely abrasive consistency and said second region has a coarsely abrasive consistency.

10. The invention of claim 8, wherein said first and third regions have a coarsely abrasive consistency and said second region has a finely abrasive consistency.

11. The invention of claim 1, wherein said degrees of abrasiveness merge into one another in said transition zone having an abrasive consistency which varies from the consistency of one region to the consistency of the other region.

12. The invention of claim 1, wherein said degrees of abrasiveness merge into one another in said transition zone wherein the degree of abrasiveness abruptly changes from one degree to the other.

* * * * *